United States Patent
Sharpless et al.

[11] Patent Number: 5,929,252
[45] Date of Patent: Jul. 27, 1999

[54] AZIRIDINATION OF OLEFINS

[75] Inventors: K. Barry Sharpless, La Jolla, Calif.; Jae Uk Jeong, Blue Bell, Pa.

[73] Assignee: The Scripps Research Institute, La Jolla, Calif.

[21] Appl. No.: 09/097,845

[22] Filed: Jun. 15, 1998

[51] Int. Cl.$^6$ ...................... C07D 203/02; C07D 203/08
[52] U.S. Cl. ............................... 548/968; 518/969
[58] Field of Search ............................ 514/183; 548/968, 548/969

[56] References Cited

PUBLICATIONS

Hassner et al., "The Reduction of Beta–Iodo Azides. A Stereospecific Synthesis of Aziridines," J. Am. Chem. Soc., vol. 91, No. 18, pp. 5046–5054, Aug. 27, 1969.

Atkinson, et al., "Aziridination of Cyclohex–2–en–1–ol and Geraniol: Comparison with Epoxidation", J. Chem. Soc., Chem. Commun., 624 (1988).

Evans, et al., "Copper–Catalyzed Aziridination of Olefins by (N–(p–Toluenesulfonyl)imino)phenyliodinane", J. Org. Chem., 56:6744 (1991).

Evans, et al., "Bis(oxazoline)–Copper Complexes as Chiral Catalysts for the Enantioselective Aziridination of Olefins", J. Am. Chem. Soc., 115:5328 (1993).

Li, et al., "Asymmetric Alkene Aziridination with Readily Available Chiral Diimine–Based Catalysts", J. Am. Chem. Soc., 115:5326 (1993).

Lowenthal, et al., "Asymmetric Copper–Catalyzed Cyclopropanation of Trisubstituted and Unsymmetrical cis–1, 2–Disubstituted Olefins: Modified Bis–Oxazoline Ligands", Tetrahedrwon Leters, 32(50):7373 (1991).

Mansuy, et al., "Iron– and Manganese–porphyrin Catalysed Aziridination of Alkenes by Tosyl– and Acyl–iminoiodobenzene", J. Chem. Soc., Chem. Commun., 1161 (1984).

Nishikori, et al., "Catalytic and Highly Enantioselective Aziridination of Styrene Derivatives", Tetrahedron Letters, 37(51):9245 (1996).

Osborn, et al., "The Asymmetric Synthesis of Aziridines", Tetrahedon: Asymmetry, 8(11):1693 (1997).

Sodergren, et al., "Preparation and Evaluation of Nitrene Precursors (PhI=NSO2Ar) for the Copper–Catalyzed Aziridination of Olefins", Tetrahedron Letters, 38(39):6897 (1997).

Vedejs, et al., "Synthesis of N–Methoxy and N–H Aziridines from Alkenes", Tetrahedron Letters, 33(23):3261 (1992).

Primary Examiner—Johann Richter
Assistant Examiner—Jane C. Oswecki
Attorney, Agent, or Firm—Donald G. Lewis

[57] ABSTRACT

A method for the direct aziridination of olefins as well as a wide range of allylic alcohols employs phenyltrimethylammonium tribromide (PTAB) as a general and effective catalyst and N-sodio-N-chloro sulfonamides, chloramine salts, as the nitrogen source.

5 Claims, 8 Drawing Sheets

TsNClNa
―――――――→
10 mol% PTAB
CH₃CN, 25 °C
12h

FIG. 1

| entry | olefin | product | yield (%)[b] | m.p. (°C)[c] |
|---|---|---|---|---|
| 1 | ⁀⁀= | ⁀⁀NTs | 93 (90) | 69-70 |
| 2 | Ph⁀= | Ph⁀NTs | 76 (62) | 85-87 |
| 3 | ⁀⁀= | ⁀⁀NTs | 95 (88) | d |
| 4 | Ph⁀= | Ph⁀NTs | 89 (72) | 82-83 |
| 5 | (cyclopentene) | (NTs) | 86 (80) | 71-72 |
| 6 | ⁀()8= | ⁀()8NTs | 54 | d |
| 7 | Ph/= | Ph/NTs | 68 (65) | 88-89 |
| 8 | ⁀()3= | ⁀()3NTs | 76 (60) | d |
| 9 | (methylcyclohexene) | (NTs) | 51 | 90-91 |

| entry | olefin | product | yield (%)[b] | m.p. (°C) |
|---|---|---|---|---|
| 1 | ⁀⁀⁀OH (trans) | ⁀⁀⁀(NTs)OH | 97 | e |
| 2 | ⁀⁀⁀OH (cis) | ⁀⁀⁀(NTs)OH | 95 | e |
| 3 | Ph⁀⁀OH | Ph⁀(NTs)⁀OH | 70 | e |
| 4 | ⁀⁀⁀⁀OH (Me) | ⁀⁀⁀⁀(NTs)OH | 73 | e |
| 5 | (Me)₂C=CH-CH₂OH | (Me)₂C(NTs)-CH-CH₂OH | 94 | 63-64 |
| 6 | ⁀OH | (NTs)⁀OH | 30[c] | e |
| 7 | CH₂=C(Me)CH₂OH | (NTs)C(Me)CH₂OH | 70[d] | e |
| 8 | PhCH₂O⁀⁀OH | PhCH₂O⁀(NTs)⁀OH | 80 | e |
| 9 | cyclohexenol | cyclohexanol-NTs (aziridine) | 87[f] | e |

| entry | olefin | product | yield |
|---|---|---|---|
| 1 | (allyl) | NTs aziridine | 35% |
| 2 | (diene) | NTs aziridine | 42% |
| 3 | (benzene) | NTs bicyclic | 40% |
| 4 | OH allyl alcohol | TsN / OH + Ts-N aziridine | 64% |
| 5 | OH | OH + Ts-N aziridine | 63% |
| 5 |  |  | 45% |
| 6a | OH | OH + Ts-N aziridine | 8% | a 2.5 eq. of chloramine-T was used.

A
AZIRIDINATION OF OLEFINS

GOVERNMENT RIGHTS

This invention was made with government support under Grant No. GM 28384 awarded by the National Institutes of Health and under Grant No. CHE 9521152 awarded by the National Science Foundation. U.S. government has certain rights in the invention.

FIELD OF THE INVENTION

The invention relates to methods for the direct aziridination of olefins. More particularly, the method relates the use of phenyltrimethyl-ammonium tribromide (PTAB) as the main group element catalyst for the direct aziridination of olefins with N-sodio-N-chloro-sulfonamides as the nitrogen source.

BACKGROUND

Aziridines are versatile building blocks in organic synthesis due to their ability to undergo highly regio- and stereoselective ring-opening reactions to give diverse nitrogen containing compounds (Tanner et al. *Angew. Chem. Int. Ed. Engl.* 1994, 33, 599; Maligres et al. *Tetrahedron Lett.* 1997, 5253). Several efforts toward developing a direct aziridination of unfunctionalized olefins using transition metal catalysts have been made (Kwart et al. *J. Am. Chem. Soc.* 1967, 89, 1951; Mansuy et al. *J. Chem. Soc., Chem. Comm.* 1984, 1161; Evans et al. *J. Org. Chem.* 1991, 56, 6744; Vedejs et al. *Tetrahedron Lett.* 1992, 3261; Södergren et al. *Tetrahedron Lett.* 1997, 6897).

In 1984, Mansuy reported a Fe(III)- and Mn(III)-porphyrin-catalyzed aziridination of unfunctionalized olefins with (N-(p-toluenesulfonyl)imino)phenyliodinane (PhI=NTs). Subsequently, Evans reported a copper-catalyzed aziridination of unfunctionalized olefins with PhI=NTs, and the asymmetric version of this reaction was later developed by the employment of chiral ligands (Lowenthal et al. *Tetrahedron Lett.* 1991, 7373; Li et al. *J. Am. Chem. Soc.* 1993, 115, 5326; Evans et al. *J. Am. Chem. Soc.* 1993, 115, 5328; Nishikori et al. *Tetrahedron Lett.* 1996, 9245; Osborn et al. *Tetrahedron: Asymmetry* 1997, 8, 1693).

Also, the direct aziridination of allylic alcohols has been reported using quinazolones as the nitrogen source in the presence of lead tetraacetate as a catalyst (Atkinson et al. *J. Chem. Soc., Chem. Comm.* 1988, 624). Although the reaction conditions for aziridination with PhI=NTs and quinazolones as the nitrene precursors are relatively mild and effective, much better methods for direct aziridination of olefins are needed before this transformation can be regarded as useful, even for laboratory-scale synthesis. The use of PhI=NTs is limited due to its complexity of preparation from (diacetyliodo)benzene and instability due to its high reactivity.

Our interest in the development of more efficient olefin oxidation processes has lead us to seek a general catalytic aziridination of olefins. What is needed, therefore, is an economically accessible method for the direct aziridination of olefins. Furthermore, what is needed is a stable and effective catalyst for the direct aziridination of olefins with a practical nitrogen source.

BRIEF SUMMARY OF THE INVENTION

The invention relates to the use of phenyltrimethylammonium tribromide (PTAB) as a general and effective catalyst for the direct aziridination of olefins as well as for a wide range of allylic alcohols with chloramine salts.

One aspect of the invention is directed to a one pot method for synthesizing an aziridine from an olefin. The method employs the step of catalyzing the addition of a nitrogen source to the olefin with a catalytic amount of phenyltrimethylammonium tribromide as the catalyst for producing the aziridine. In a preferred mode, the nitrogen source is a N-sodio-N-chloro-sulfonamide. A preferred N-sodio-N-chloro-sulfonamide is selected from p-NO$_2$PhSO$_2$NClNa, n-BuSO$_2$NClNa, MeSO$_2$NClNa, t-BuSO$_2$NClNa, and an N-sodio-N-chloro salt of a sulfonamide represented by one of the following structures:

In the above structures, R, R' and R" are each independently a radical selected from hydrogen, —O—(C$_1$-C$_6$ alkyl), —(C$_1$-C$_6$ alkyl), —O-benzyl, —O-phenyl, —NO$_2$, —Cl, —Br, —I, methyl; -methoxy, t-Butyl, and CF$_3$. Preferred organic solvents include acetonitrile, DMF, DMSO, THF, acetonitrile and water cosolvent, acetonitrile and DMF cosolvent, acetonitrile and DMSO cosolvent and acetonitrile and THF cosolvent.

More particularly, the one pot method may commence by admixing the olefin with a nitrogen source and an organic solvent for forming a reaction mixture. The addition of the nitrogen source to the olefin is then catalyzed with phenyltrimethylammonium tribromide as the catalyst wherein a bromide group of the catalyst adds beta to the nitrogen group of said nitrogen source for forming a β-bromo-N-substituted intermediate. The β-bromo-N-substituted intermediate is then cyclized by intramolecular displacement of the β-bromo group with the nitrogen group of said β-bromo-N-substituted intermediate for forming the aziridine.

Another aspect of the invention is directed to a composition of matter which includes an olefin, an organic solvent, a nitrogen source, and a catalytic amount of phenyltrimethylammonium tribromide as a catalyst for catalyzing an aziridination of said olefin.

DETAILED DESCRIPTION OF THE INVENTION

Figure 1:
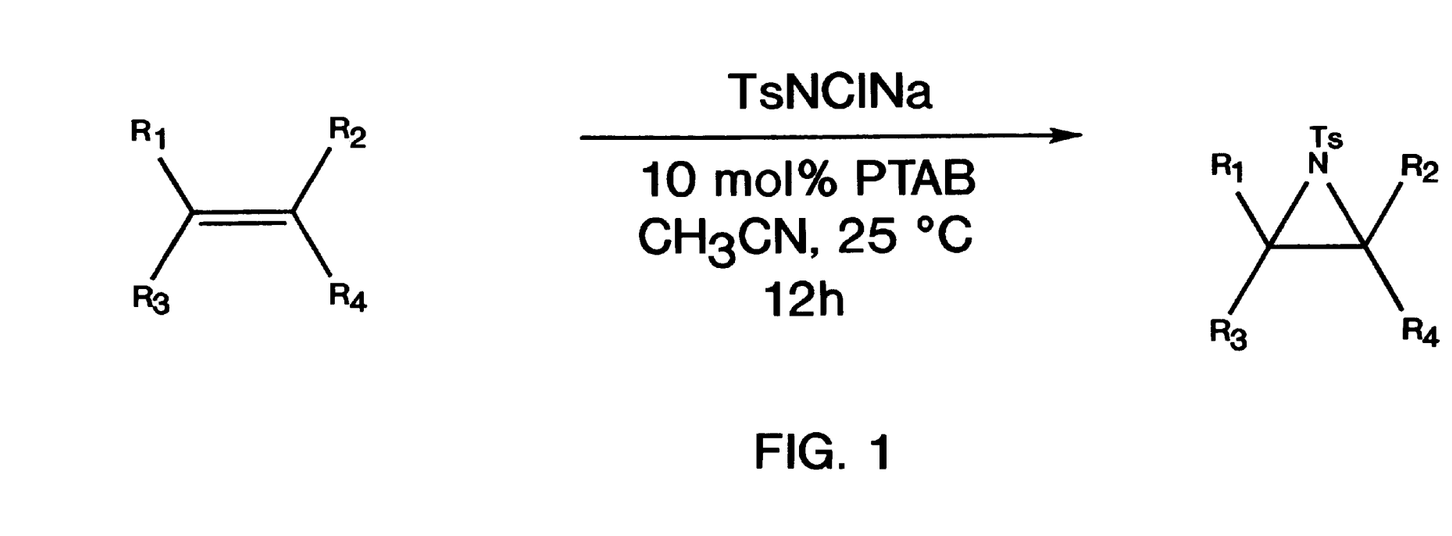
FIG. 1 illustrates the described method which involves the direct aziridination of olefins using phenyltrimethylammonium tribromide (PTAB) as a general and effective catalyst and chloramine salts as a practical nitrogen source: The following represents typical R groups which functionalize the olefin as shown in FIG. 1: a) Ronosubstituted olefins: R$_1$=R$_2$=R$_3$=H, and R$_4$=alkyl or aryl or CH$_2$OH or CH$_2$OR (Ac, Me, R'$_3$Si, etc.); b) disubstituted olefins: (i) cis: R$_1$=R$_3$=H, R$_2$=alkyl, and R4=alkyl or aryl or CH$_2$OH or CH$_2$OR (Ac, Me, R'$_3$Si, etc.). (ii) trans: R$_1$=alkyl, R$_2$=R$_3$=H, and R4=alkyl or aryl or CH$_2$OH or CH$_2$OR (Ac, Me, R'$_3$Si, etc.). (iii) cyclic: R$_1$=R$_3$=H, R$_2$=R$_4$=(CH$_2$)$_n$ (iv) 1, 1-: R$_1$=R$_2$=H, R$_3$=alkyl, and R4=alkyl or aryl or CH$_2$OH or CH$_2$OR (Ac, Me, R'$_3$Si, etc.); c) trisubstituted olefins: R$_1$=R$_3$=alkyl, R$_2$=H , and R4 alkyl or aryl or CH$_2$OH or CH$_2$OR (Ac, Me, R'$_3$Si, etc.) or R$_1$=R$_2$=alkyl, R$_3$=H and R4=alkyl or aryl or CH$_2$OH or CH$_2$OR (Ac, Me, R'$_3$Si, etc.); d) tetrasubstituted: R$_1$=R$_2$=R$_3$=R$_4$=alkyl.

The need for the development of more efficient olefin oxidation processes has led us to seek a direct, general catalytic aziridination of olefins. Unreported studies, from our group, demonstrated that metal bromides (HgBr2, CuBr2, and FeBr2), molecular bromine (Br2), and NBS served as catalysts for the aziridination of unfunctionalized olefins with chloramine-T trihydrate (TsNClNa.3H$_2$O) as the nitrogen source in the presence of molecular sieves 4 Å, but still suffered from a lack in substrate scope. Herein, we disclose that phenyltrimethylammonium tribromide (PTAB) is a general and effective catalyst for the direct aziridination of olefins as with chloramine salts as the nitrogen source (FIG. 1). We have found that the method works best for the following olefins which have typical R groups as shown in FIG. 1. The employable range of substrate scope is as follows: a) monosubstituted olefins: R$_1$=R$_2$=R$_3$=H, and R$_4$=—(C$_1$-C$_6$ alkyl), -benzyl, -phenyl or CH$_2$OH or CH$_2$OR (Ac, Me, —(C$_1$-C$_6$ alkyl/or aryl)$_3$Si, etc.); b) disubstituted olefins: (i) cis: R$_1$=R$_3$=H, R$_2$=alkyl, and R4=alkyl or aryl or CH$_2$OH or CH$_2$OR (Ac, Me, R'$_3$Si, etc.). (ii) trans: R$_1$=alkyl, R$_2$=R$_3$=H, and R4=alkyl or aryl or CH$_2$OH or CH$_2$OR (Ac, Me, R'$_3$Si, etc.). (iii) cyclic: R$_1$=R$_3$=H, R$_2$=R$_4$=(CH$_2$)$_n$ (iv) 1, 1-: R$_1$=R$_2$=H, R$_3$=alkyl, and R4=alkyl or aryl or CH$_2$OH or CH$_2$OR (Ac, Me, R'$_3$Si, etc.); c) trisubstituted olefins: R$_1$=R$_3$=alkyl, R$_2$=H, and R4=alkyl or aryl or CH$_2$OH or CH$_2$OR (Ac, Me, R'$_3$Si, etc.) or R$_1$=R$_2$=alkyl, R$_3$=H , and R4=alkyl or aryl or CH$_2$OH or CH$_2$OR (Ac, Me, R'$_3$Si, etc.); d) tetrasubstituted olefins: R$_1$=R$_2$=R$_3$=R$_4$=alkyl.

EXAMPLE 1

Bromine-Catalyzed Aziridination of Olefins with Chloramine-T. A rare example of Atom-Transfer Redox Catalysis by a Main Group Element The invention relates to a direct method of synthesis of aziridines using phenyltrimethylammonium tribromide (PTAB) as a general and effective catalyst for the direct aziridination of functionalized olefins (see above discussion for olefin substrate scope) as well as a wide range of allylic alcohols with chloramine salts as the nitrogen source.

Tyical conditions for olefins employ 10 mol % of PTAB, 1.1 eq. of anhydrous chloramine-T in acetonitrile (0.2M; purified by Grubbs' method; Pangborn et al. *Organometallics*, 1996, 15, 1518) at room temperature for 4–12 hours. The commercially available chloramine-T trihydrate (other nitrogen sources can be substituted—see list below) was dried to constant weight at 60° C. for 12 hours under vacuum over P2O5. We recommend against using a vacuum oven for this purpose, due to the possibility of an explosion. For details, see Sharpless, K. B.; Hori, T.; Truesdale, L. K.; Dietrich, C. O. *J. Am. Chem. Soc.* 1976, 98, 269.

Figure 2:
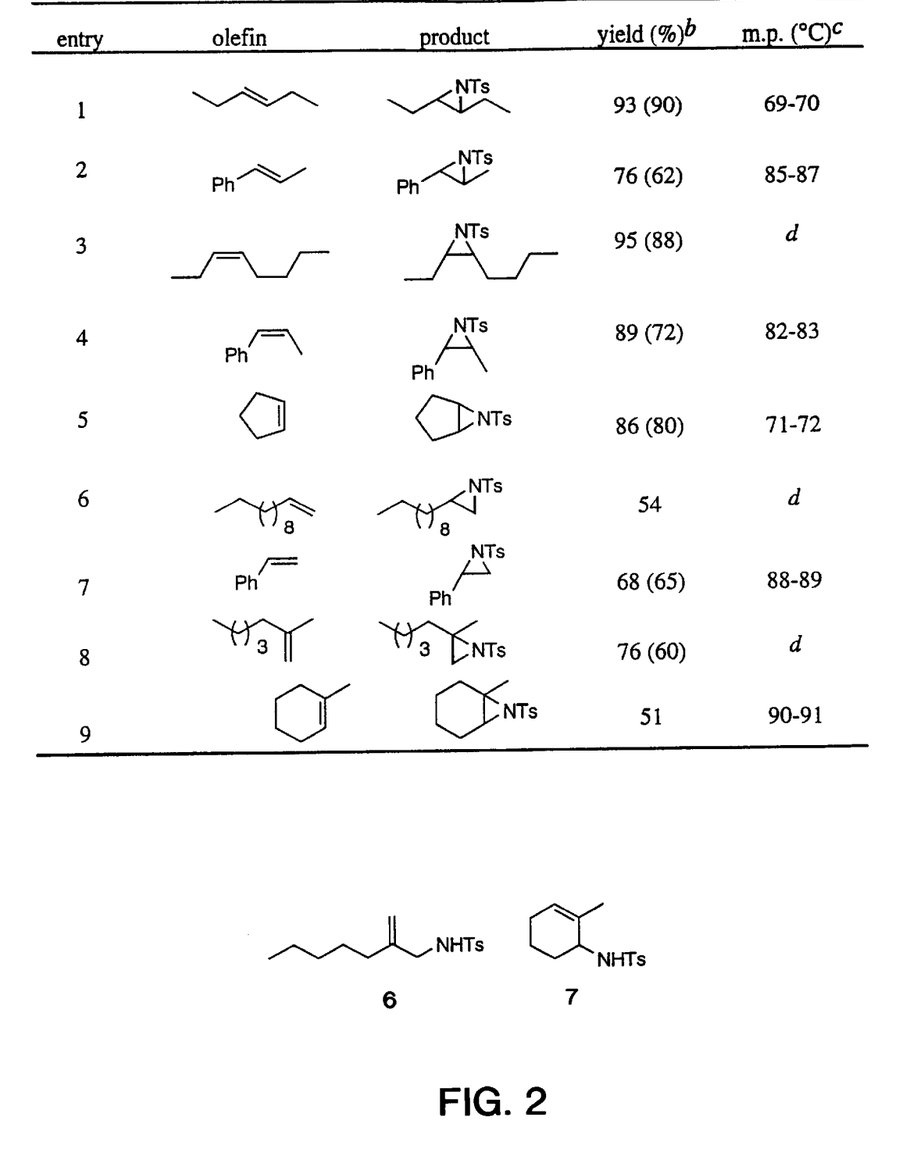
FIG. 2 provides representative examples of 1,2-disubstituted olefins which provided the corresponding aziridines stereospecifically in excellent yields.

The role of PTAB is two fold. It functions first as the source of the positive bromine species (Br–X) which initiates the catalytic cycle and second as a solid-liquid phase transfer catalyst to enhance the dissolution of chloramine-T in acetonitrile. As depicted in FIG. 2 (All aziridines were characterized by $^1$H and $^{13}$C NMR and by HRMS) 1,2-disubstituted olefins (FIG. 2, entries 1–5) provided the corresponding aziridines stereospecifically and in excellent yields. Higher initial olefin concentration with anhydrous chloramine-T in acetonitrile did not affect the yield of the aziridine; at 0.5M in olefin, the reaction of trans-β-methylstyrene (entry 2) gave a 71% yield of the desired aziridine. Monosubstituted olefins (entries 6 and 7) also gave modest yields of the aziridines.

The reaction of 2-methyl-1-heptene (entry 8) afforded a 76% yield of the desired aziridine along with 10% of the allylic sulfonamide 6 that is likely formed from an elimination process which competes with aziridine ring-closure. Even a sterically hindered olefin such as a trisubstituted olefin (entry 9) gave 51% of the corresponding aziridine. The reaction of 1-methyl-1-cyclohexene also provided the allylic sulfonamide 7 in 5%, as was observed for the 1,1-disubstituted olefin (entry 8) as in case of which has a methyl group at the vinyl position.

Good yields were also obtained using the commercially available form of chloramine-T, which is a trihydrate (TsNClNa.3H$_2$O), with 10 mol % of PTAB in acetonitrile (0.2M olefin concentration) at room temperature. However, in contrast to the aziridination with anhydrous chloramine-T, higher olefin concentration with chloramine-T trihyrate gave lower yields of the aziridines. For example, the reaction of cyclopentene gave a 55% yield with chloramine-T trihyrate at 0.5M olefin concentration. Interestingly, molecular sieves did not affect the reaction. To represent the applicability of this reaction to large scale processes, a 0.5 mol scale reaction of cyclopentene (34 g) was undertaken with TsNClNa.3H$_2$O (155 g) and 10 mol % PTAB (19 g) in CH$_3$CN (2.5L). The aziridination product (95 g, 80%) was easily isolated by crystallization of the crude reaction mixture after aqueous work-up followed by filtration through a 15 cm×15 cm plug of silica gel (1:1:10 EtOAc:CH$_2$Cl$_2$:Hexane).

Figure 3:
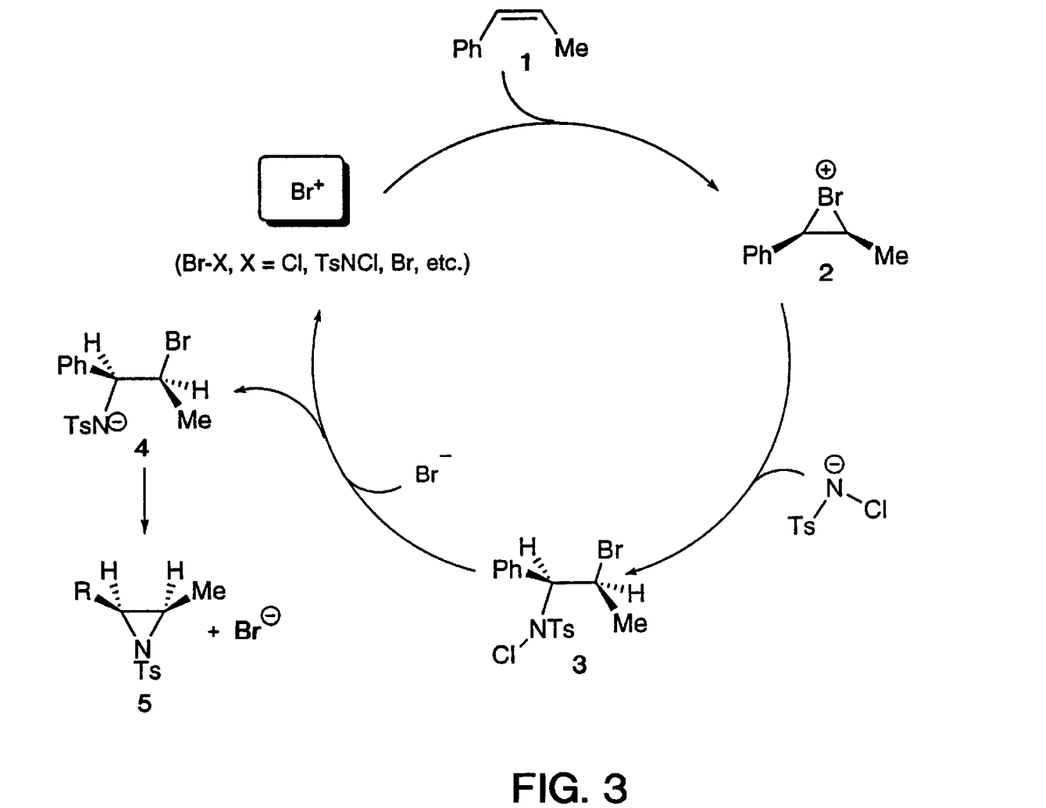
FIG. 3 shows the essential details of the general mechanism for the bromine-catalyzed aziridination process in the case of cis-β-methylstyrene 1.

The essential details of the general mechanism for this bromine-catalyzed aziridination process are shown in FIG. 3 for the case of cis-β-methylstyrene 1. First, the olefin reacts with a Br+ source to give bromonium ion 2, which is opened by TsNCl− forming the β-bromo-N-chloro-N-toluenesulfonamide 3. The bromonium ion 2 and the key intermediate 3 have been also found on the reaction of N, N-dihalosulfonamides with olefins, see: Mirskova et al. *Russ. Chem. Rev.* 1989, 58, 250. Studies have established that chloramine-T is an exceptionally good nucleophile (Campell et al. *Chem. Rev.* 1978, 78, 65. In most other cases, TsNCl− should attack the less hindered position). The adduct 3 is then reduced to the intermediate 4 by Br− ion (or chloramine-T) followed by cyclization to the aziridine 5. The resultant Br−X species from the aziridine formation then acts as a source of Br+ ion to initiate another cycle of aziridination.

Figure 4:
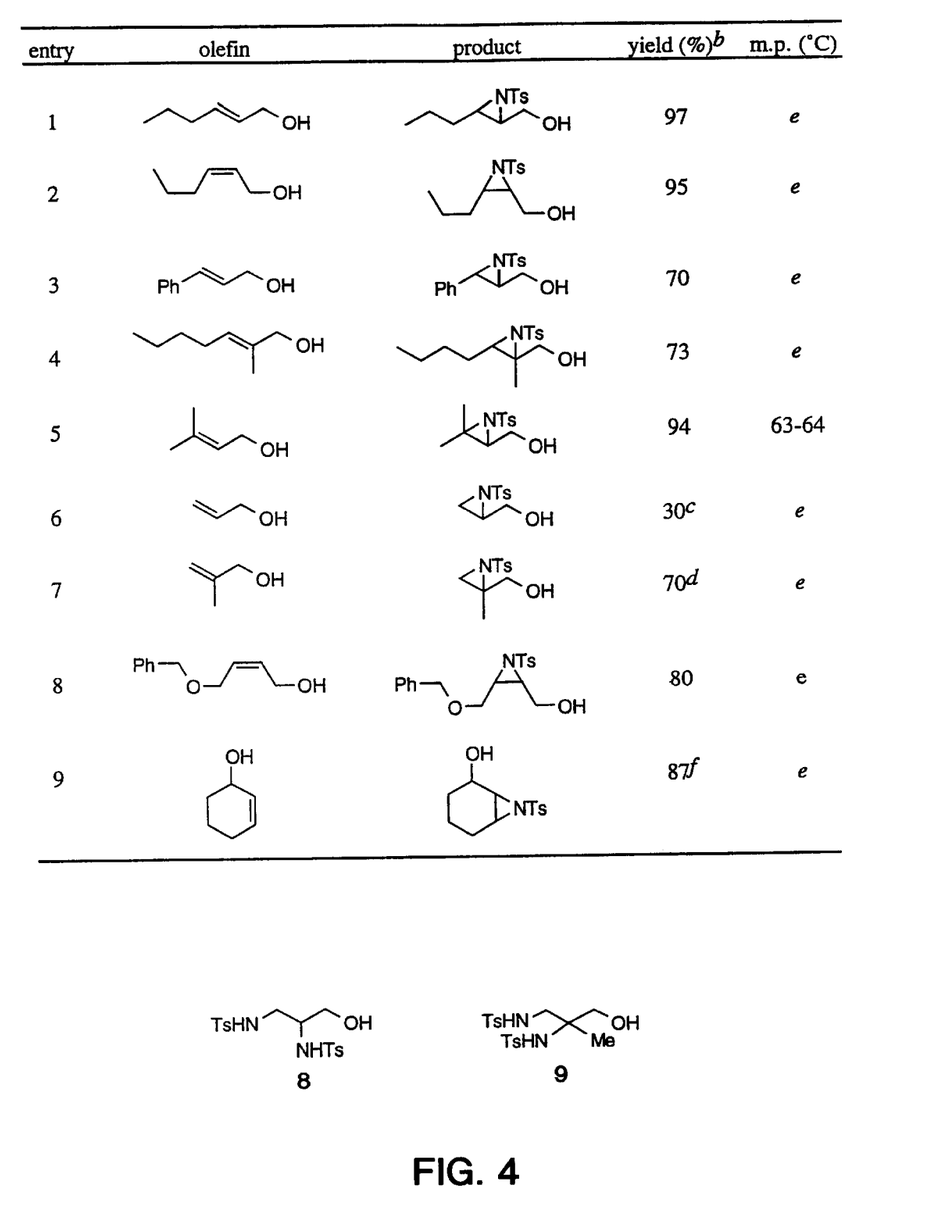
FIG. 4 provides further representative examples of allylic alcohols which provided the corresponding aziridines stereospecifically in excellent yields.

Bromine-catalyzed aziridination with anhydrous chloramine-T proceeds very effective for di- and tri-substituted allylic alcohols, resulting in yields of up to 97% (FIG. 4, entries 1–5). A possible rationale for the hydroxyl group-effect is that hydrogen-bonding to the anionic chloramine-T helps ferry it in for nucleophilic attack on the bromonium ion. In the case of allyl alcohol (entry 6) 30% of the 1,2-disulfonamide 8 is also produced. This is not surprising since TsNCl− is an excellent nucleophile and the primary product, an aza-glycidol analog, should be a reactive electrophile. However, the reaction of 2-methyl-2-propen-1-ol (entry 7) gave the corresponding aziridine in a 70% yield with 12% of disulfonamide 9.

When the latter two reactions (entries 6 and 7) were carried out with 2.2 eq. of anhydrous chloroamine-T, the disulfonamide products 8 and 9 were obtained in 60% and 62% yield, respectively, without any aziridination products. The likelihood that hydrogen bonding is important is more clearly evident in the outcome for 2-cyclohexen-1-ol (entry 9). Examination of the 1H NMR of the crude product indicates a diastereoselectivity of 2.5:1 in favor of the syn-aziridination product. The assignment of the configuration of the diastereomers was accomplished by comparing the coupling constant with the corresponding aziridine of cyclohex-2-ene-1-ol.

Electron deficient olefins such as α,β-unsaturated esters and amides are beyond the scope of this reaction. In summary, we have found a simple bromine-catalyzed process for preparing N-sulfonyl aziridines directly from olefins using $RSO_2NCl-$ salts as the nitrenoid source. See example 2 for nitrenoid sources other than chloramine-T which are employable with the process. Chloramine-T (TsNClNa) is especially convenient due to its ready availability and to the tendency of the derived aziridines to be crystalline. Since the process can run at reasonable concentration (e.g. 0.5M) and in the case of crystalline products entails a very easy work-up/isolation sequence, large scale applications can be considered. Even the aziridines from this process are only racemic but still attractive for diversity applications.

EXAMPLE 2

Figure 5:
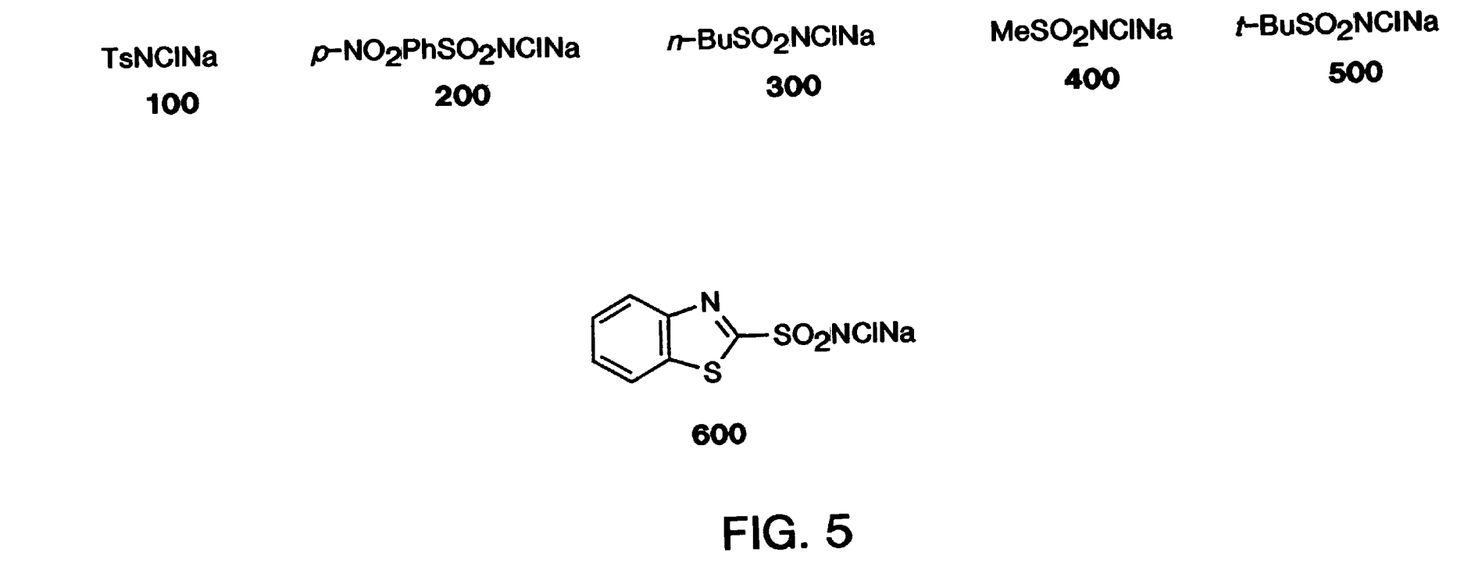
FIG. 5 shows other nitrogen sources which include p-NO$_2$PhSO$_2$NClNa, n-BuSO$_2$NClNa, MeSO$_2$NClNa, and t-BuSO$_2$NClN. Results indicate that these sources are also successful in achieving good product yields.

General Conditions for Aziridination using PTAB and other nitogen sources, temperatures, solvent conditions with a broad range of olefins Other nitrogen sources include $p-NO_2PhSO_2NClNa$, $n-BuSO_2NClNa$, $MeSO_2NClNa$, and $t-BuSO_2NClNa$. Results indicate that these sources are also successful in achieving good product yields (FIG. 5). The N-Tosyl group is somewhat difficult to deprotect (Yasuhara, et al. *Tetrahedron Lett.* 1998, 595), so more labile nitrogen sources (Maligres et al. *Tetrahedron Lett.* 1997, 5253; Vedejs et al. *J. Am. Chem. Soc.* 1996, 118, 9796) are useful with the process. The above nitrogen sources provide moderate to excellent yields of the corresponding aziridines (FIG. 6), depending on substrate used.

Figure 7:
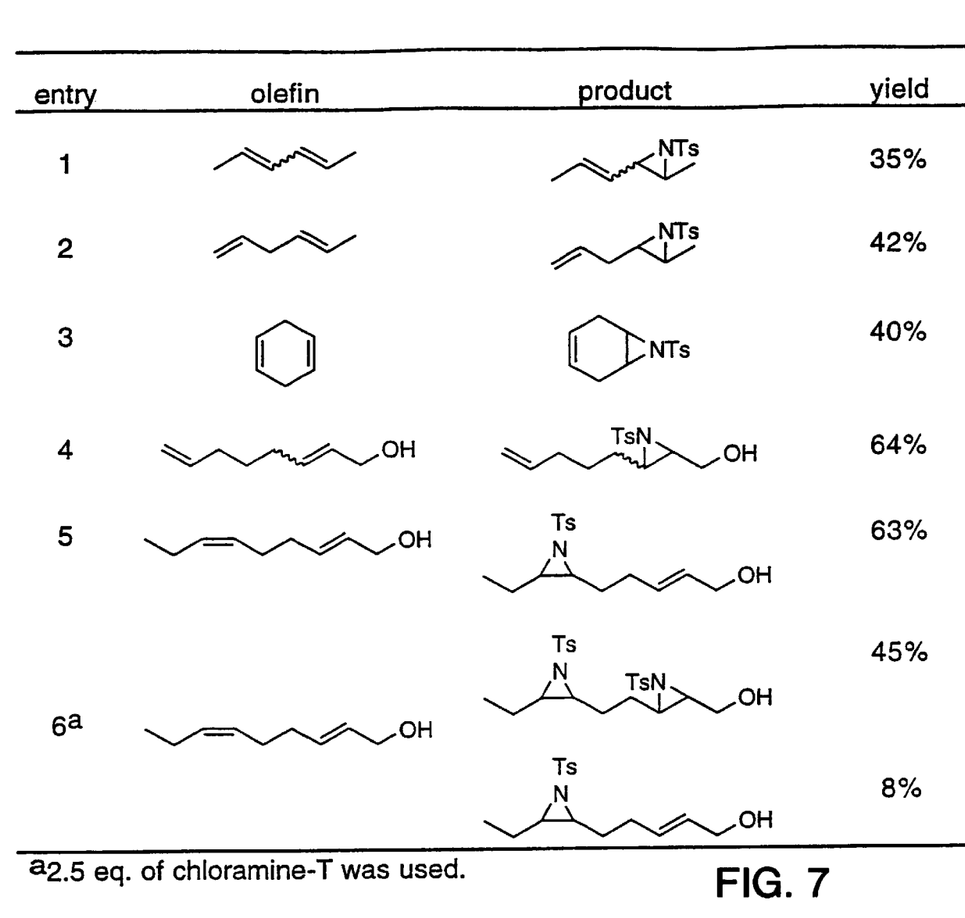
FIG. 7 provides representative examples of allyllic and disubstituted olefins using other nitrogen sources achieving good product yields.

Sulfonamides such as $RSO_2NClNa$ wherein R=alkyl and R=aryl can be used in lieu of chloramine T in the general procedure. A further sulfonamide embodiment as the nitrogen source comprises the N-sodio-N-chloro salt of a compound represented by the following structure:

wherein R, R' and R" are each independently a radical selected from a group consisting of hydrogen, —O—($C_1$–$C_6$ alkyl), —($C_1$–$C_6$ alkyl), —O-benzyl, —O-phenyl, —$NO_2$, —Cl, —Br, —I, methyl; -methoxy, t-Butyl, and CF3. Other sulfonamides which can be substituted in lieu of chloramine T using the general method, described below, are the hetreoarene-2-sulfoneamides as represented by the following structures:

Vinyl aziridines are useful precursors for β-lactams and allylic amines, which can be obtained by the aziridination of conjugated dienes (Knight, J. G.; Muldowney, M. P. *Synlett.* 1995, 949). The general procedure (vide infra) gave moderate yields of aziridines (FIG. 7). The reactions of 1.1 eq. of chloramine-T with diene gave monoaziridines. The allylic alcohol which has terminal olefin (entry 4) was converted to the allylic aziridine without bis-aziridine in the standard condition. But the allylic alcohol which has cis olefin (entry 5) was converted to the simple aziridine instead of the allylic aziridine. The reaction of 2.5 eq. of chloramine-T with the allylic alcohol which has cis olefin (entry 6) gave bisaziridination product as a major.

Figure 8A:
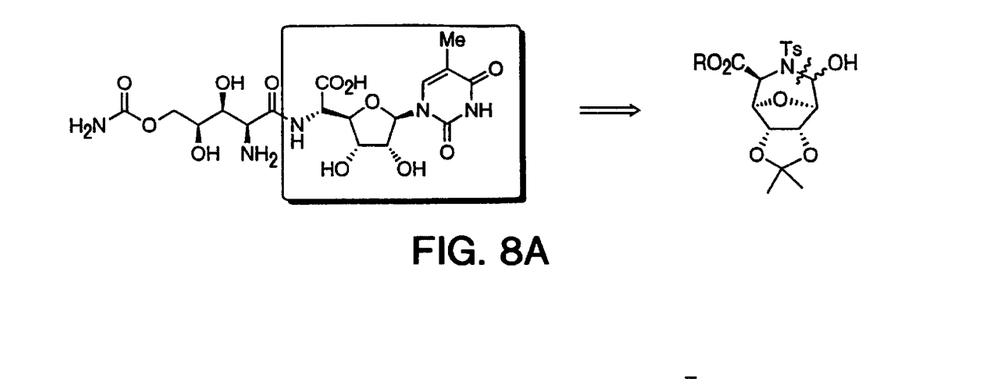
FIG. 8 shows that the direct and regioselective synthesis of aziridination opens the door to biologically active compounds (equation A). The combination of aziridination and asymmetric epoxidation or asymmetric dihydroxylation is a useful tool for the synthesis of key structural intermediates (equations B and C) of natural products like the synthesis of nucleoside structure of polyoxin J (equation A).
Figure 8B:
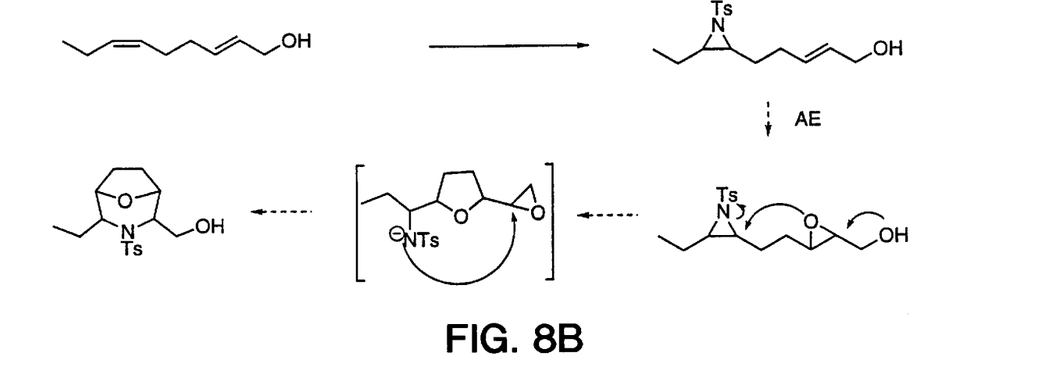
Figure 8C:
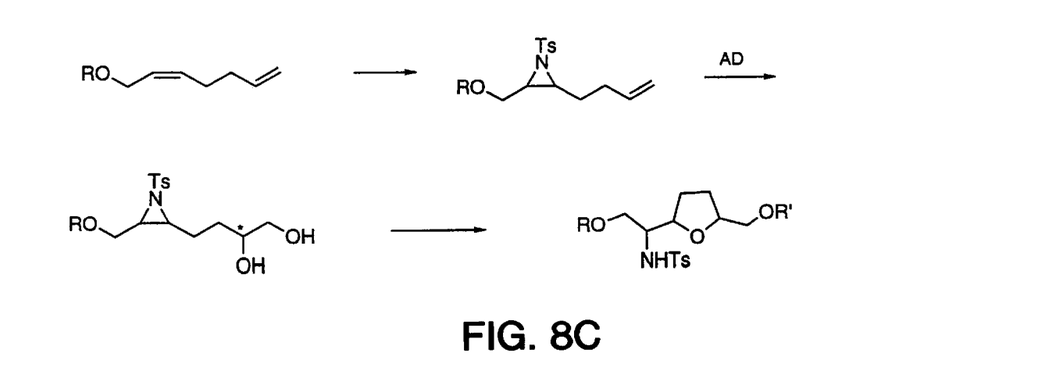

This regioselectivity of aziridination initiates the application to the synthesis of biologically active compounds. The combination of aziridination and asymmetric epoxidation or asymmetric dihydroxylation is a useful tool for the synthesis of key structure of natural products like the synthesis of nucleoside structure of polyoxin J (Gethin et al. *Tetrahedron* 1997, 53, 14417) which is a nucleoside inhibitor (FIG. 8).

General solvent conditions for the synthesis of the aziridines include the following (using the molar range specified in the general procedure): 1) acetonitrile, no cosolvent 2) acetonitrile in 5–15% water cosolvent or (using MeOH, EtOH or t-BuOH as a cosolvent in lieu of water); 3) DMF, no cosolvent; 4) DMSO, no cosolvent; 5) THF, no cosolvent;

and 6) acetonitrile in 5–25% DMF, DMSO or THF cosolvent. Any of the above conditions can be substituted in lieu of that which is specified in the general procedure as described below.

Temperature conditions for the aziridine process varies from 60° C. to 25° C. for reactions with N-sodio-N-chlorosulfonamides and PTAB primarily in organic solvents.

While a preferred form of the invention has been shown in the drawings and described, since variations in the preferred form will be apparent to those skilled in the art, the invention should not be construed as limited to the specific form shown and described, but instead is as set forth in the following claims.

Synthetic Protocols

General: $^1$H and $^{13}$C nmr spectra were recorded either on a Bruker AM-250, a Bruker AMX-400 or a Bruker AMX-500 spectrometer. Residual protic solvent CHCl$_3$ ($\delta_H$=7.26 ppm, $\delta_c$=77.0), d$_4$-methanol ($\delta_H$=3.30 ppm, $\delta_c$=49.0) and D$_2$O ($\delta_H$=4.80 ppm, $\delta_c$ (of $\underline{C}$H$_3$CN)=1.7 ppm) or TMS ($\delta_H$=0.00 ppm) were used as internal reference. Coupling constants were measured in Hertz (Hz). HRMS were recorded using FAB method in a m-nitrobenzylalcohol (NBA) matrix doped with NaI or CsI. Infra-red spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel F$_{254}$) and visualized by cerium molybdophosphate or ninhydrin. Diethyl ether, tetrahydrofuran (THF) and toluene (PhCH$_3$) were distilled from sodium-benzophenone ketyl, dichloromethane (DCM) and acetonitrile from calcium hydride. Other solvents and reagents were purified by standard procedures if necessary.

General procedure (described for trans-3-hexene) as illustrated in FIG. 2, entry 1: To a mixture of trans-3-hexene (252 mg, 3 mmol; see above discussion for employable olefins (FIG. 1); 1.0 equivalents used) and anhydrous N-sodio-N-chloro sulfonamide (chloramine T/751 mg, 3.3 mmol; see above discussion for employable salts or chloramine trihydrates (chloramine T trihydrate can be effectively used in the same concentration); effective range: 1.0–2.0 equivalents; optimal concentration 1.1 equivalents) in CH3CN (15 ml, 0.2 Molar; see above discussion for employable solvents; effective range: 0.01 Molar to 1.0 Molar) was added PTAB (113 mg, 0.3 mmol; effective range: 0.05 to 0.50 equivalents; optimal concentration: 0.10 equivalents) at 25° C. (effective range 25° C. to 60° C.). After vigorous stirring for 12 h (time can vary from 1 h- to 24 h depending on scale and substrate). The reaction mixture was worked up using standard workup conditions. A typical procedure may be carried out as follows: The reaction mixture was concentrated (about up to 1/10 volume) and filtered through a short column of silica gel (4×4 cm, 10% EtOAc in hexane). After evaporation of the solvent, the resultant solid was purified by recrystallization in hexane to give 710 mg (93%) of trans-2,3-diethyl-1-[(4-methylphenyl)sulfonyl]aziridine as colorless crystals; 1H NMR (CDCl3400 MHz)δ7.81 (d, J=8.2 Hz, 2H), 7.28 (d, J=8.2 Hz, 2H), 2.56–2.61 (m, 2H), 2.40 (s, 3H), 1.63–1.79 (m, 4H), 0.90 (t, J=7.5 Hz, 6H); 13C NMR (CDCl3, 100 MHz) d 143.7, 137.9, 129.4, 127.4, 50.9, 23.2, 21.5, 11.7; MS (FAB, NBA/NaI): 254 (M+H)+; HRMS (FAB, NBA/NaI): calculated for C13H19NO2S (MNa)+ 276.1034, found 276.1029; m.p. 69–70° C. (hexane).

Modified work-up of the General Procedure: The reaction mixture was diluted with ethyl acetate (40 ml) and water (40 ml). The organic layer was separated and washed with brine (20 ml), followed by drying over MgSO4. After filtration and evaporation, the product was purified by recrystallization or column chromatography on silica gel.

Good yields were also obtained using the commercially available form of Chloramine-T, which is a trihydrate (TsNClNa.3H20), with 10 mol % of PTAB in acetonitrile (0.2M olefin concentration) at room temperature. However, in contrast to the aziridination with anhydrous Chloramine-T, higher olefin concentration with Chloramine-T trihyrate gave lower yields of the aziridines. For example, when the trans-β-methylstyrene aziridination was run 0.5$\underline{M}$ in acetonitrile the yield was 71% (cf., 0.2$\underline{M}$, 76% yield).the reaction of cyclopentene gave a 55% yield with Chloramine-T trihyrate at 0.5$\underline{M}$ [olefin], and interestingly when this experiment was repeated in the presence of molecular sieves 4 Å the yield was unchanged. To represent the applicability of this reaction to large scale processes, a 0.5 mol scale reaction of cyclopentene (34 g) was undertaken with TsNClNa.3H20 (155 g, 0.55 mol) and 10 mol % PTAB (19 g, 0.05 mol) in CH3CN (2.5L, therefore ~0.2$\underline{M}$). The aziridination product was easily isolated by crystallization of the crude reaction mixture (95 g, 80%, m.p. 71–72° C.). While a preferred form of the invention has been shown in the drawings and described, since variations in the preferred form will be apparent to those skilled in the art, the invention should not be construed as limited to the specific form shown and described, but instead is as set forth in the following claims.

Representative Examples

Synthesis of trans-2-Methyl-1-[(4-methylphenyl) sulfonyl]-3-phenylaziridine as illustrated in FIG. 2 entry 2

Synthesized according to the general procedure as described above using the olefin, trans-propenylbenzene (Acros/Aldrich) $^1$H NMR (CDCl$_3$, 400 MHz) d 7.81 (d, J=8.3 Hz, 2H), 7.12–7.37 (m, 7H), 3.79 (d, J=4.3 Hz, 1H), 2.86–2.94 (m, 1H), 2.38 (s, 3H), 1.83 (d, J=6.0 Hz, 3H); $^{13}$C NMR (CDCl$_3$, 100 MHz) d 143.9, 137.7, 135.6, 129.6, 128.5, 128.1, 127.2, 126.3, 49.16, 49.13, 21.6, 14.1; MS (FAB, NBA/NaI): 310 (MNa$^+$); HRMS (FAB, NBA/NaI): calculated for C$_{16}$H$_{17}$NO$_2$S (M+H)$^+$288.1058, found 288.1052; m.p. 85–87° C. (1:4=EA/hexane); Anal. Calculated for C$_{14}$H$_{19}$NO$_2$S: C, 66.87; H, 5.96, found: C, 66.93; H, 5.73.

Synthesis of 2-Butyl-3-ethyl-1-[(4-methylphenyl) sulfonyl]aziridine as illustrated in FIG. 2 entry 3

Synthesized according to the general procedure as described above using the olefin, cis-3-octene (ChemSampCo) $^1$H NMR (CDCl$_3$, 400 MHz) d 7.79 (d, J=8.2 Hz, 2H), 7.29 (d, J=8.3 Hz, 2H), 2.68–2.77 (m, 2H), 2.41 (s, 3H), 1.18–1.49 (m, 8H), 0.77–0.85 (m, 6H); $^{13}$C NMR (CDCl$_3$, 100 MHz) d 144.2, 135.3, 129.5, 128.0, 46.6, 45.3, 29.4, 26.3, 22.2, 21.6, 20.1, 13.8, 11.6; MS (FAB, NBA/NaI): 282 (M+H)$^+$; HRMS (FAB, NBA/NaI): calculated for C$_{15}$H$_{23}$NO$_2$S (MNa$^+$) 304.1347, found 304.1337.

Synthesis of cis-2-Methyl-1-[(4-methylphenyl)sulfonyl]-3-phenylaziridine as illustrated in FIG. 2 entry 4

Synthesized according to the general procedure as described above using the olefin, cis-n-methylstyrene (ChemSampCo) $^1$H NMR (CDCl$_3$, 400 MHz) d 7.87 (d, J=8.3 Hz, 2H), 7.17–7.38 (m, 7H), 3.92 (d, J=7.3 Hz, 1H), 3.15–3.22 (m, 1H), 2.43 (s, 3H), 1.01 (d, J=5.8 Hz, 3H); $^{13}$C NMR (CDCl$_3$, 100 MHz) d 144.5, 135.2, 132.7, 129.7, 128.3, 127.8, 127.5, 46.1, 41.6, 21.7, 11.9; MS (FAB, NBA/NaI): 310 (MNa$^+$); HRMS (FAB, NBA/NaI): calculated for $C_{16}H_{17}NO_2S$ (M+H)$^+$288.1058, found 288.1050; m.p. 82–83° C. (1:4=EA/hexane).

Synthesis of 6-[(4-methylphenyl)sulfonyl]-6-azabicyclo[3.1.0]hexane as illustrated in FIG. 2 entry 5

Synthesized according to the general procedure as described above using the olefin, cyclopentene (Aldrich) $^1$H NMR (CDCl$_3$, 400 MHz) d 7.80 (d, J=8.3 Hz, 2H), 7.31 (d, J=8.0 Hz, 2H), 3.32 (s, 2H), 2.59 (s, 3H), 1.89–1.96 (m, 2H), 1.52–1.65 (m, 3H), 1.33–1.43 (m, 1H); $^{13}$C NMR (CDCl$_3$, 100 MHz) d 144.1, 136.0, 129.6, 127.6, 46.7, 26.9, 21.6, 19.5; MS (FAB, NBA/NaI): 260 (MNa$^+$); HRMS (FAB, NBA/NaI): calculated for $C_{12}H_{15}NO_2S$ (M+H)$^+$238.0902, found 238.0909; m.p. 71–72° C. (hexane); Anal. Calculated for $C_{14}H_{19}NO_2S$: C, 60.73; H, 6.37, found: C, 60.47; H, 6.22.

Synthesis of 1-[(4-methylphenyl)sulfonyl]-2-decylaziridine as illustrated in FIG. 2 entry 6

Synthesized according to the general procedure as described above using the olefin, 1-dodecene (Aldrich) $^1$H NMR (CDCl$_3$, 500 MHz) d 7.83 (d, J=8.0 Hz, 2H), 7.34 (d, J=8.0 Hz, 2H), 2.72 (m, 1H), 2.64 (d, J=7.0 Hz, 1H), 2.45 (s, 3H), 2.06 (d, J=4.5 Hz, 1H), 1.53 (m, 1H), 1.35–1.12 (m, 17H), 0.87 (t, J=7.0 Hz, 3H); MS (FAB, NBA/NaI): 360 (MNa$^+$); HRMS (FAB, NBA/NaI): calculated for $C_{19}H_{31}NO_2S$ (M+H)$^+$338.2154, found 338.2146.

Synthesis of 1-[(4-methylphenyl)sulfonyl]-2-phenylaziridine as illustrated in FIG. 2 entry 7

Synthesized according to the general procedure as described above using the olefin, styrene (Aldrich) $^1$H NMR (CDCl$_3$, 400 MHz) d 7.86 (d, J=8.3 Hz, 2H), 7.18–7.34 (m, 7H), 3.77 (dd, J=7.2, 4.5 Hz, 1H), 2.98 (d, J=7.2 Hz, 1H), 2.43 (s, 3H), 2.38 (d, J=4.5 Hz, 1H); $^{13}$C NMR (CDCl$_3$, 100 MHz) d 144.7, 135.0, 134.9, 129.8, 128.6, 128.3, 128.0, 126.6, 41.0, 36.0, 21.7; MS (FAB, NBA/NaI): 296 (MNa$^+$); HRMS (FAB, NBA/NaI): calculated for $C_{15}H_{15}NO_2S$ (M+H)$^+$274.0902, found 274.0898; m.p. 88–89° C. (hexane).

Synthesis of 2-Methyl-1-[(4-methylphenyl)-sulfonyl]-2-pentylaziridine as illustrated in FIG. 2 entry 8

Synthesized according to the general procedure as described above using the olefin, 2-methyl-1-heptene (Aldrich) $^1$H NMR (CDCl$_3$, 500 MHz) d 7.81 (d, J=8.3 Hz, 2H), 7.30 (d, J=8.3 Hz, 2H), 2.54 (s, 1H), 2.42 (s, 3H), 2.27 (s, 1H), 1.23–1.62 (m, 8H), 1.61 (s, 3H), 0.86 (t, J=6.9 Hz, 3H); $^{13}$C NMR (CDCl$_3$, 100 MHz) d 143.7, 138.1, 129.4, 127.2, 51.0, 41.4, 37.7, 31.5, 25.4, 22.5, 21.5, 18.5, 13.9; MS (FAB, NBA/NaI): 304 (MNa$^+$); HRMS (FAB, NBA/NaI): calculated for $C_{15}H_{23}NO_2S$ (M+H)$^+$282.1528, found 282.1521.

Synthesis of 1-Methyl-7-[(4-methylphenyl)sulfonyl]amino-7-azabicyclo[4.1.0]heptane as illustrated in FIG. 2 entry 9

Synthesized according to the general procedure as described above using the olefin, 1-methyl-1-cyclohexene (Aldrich) $^1$H NMR (CDCl$_3$, 500 MHz) d 7.83 (d, J=8.5 Hz, 2H), 7.30 (d, J=8.0 Hz, 2H), 3.06 (d, J=5.5 Hz, 1H), 2.43 (s, 3H), 2.06 (dt, J=14.5, 5.0 Hz, 1H), 1.78–1.86 (m, 1H), 1.72 (s, 3H), 1.51–1.60 (m, 2H), 1.35–1.47 (m, 2H), 1.26–1.35 (m, 1H), 1.07–1.16 (m, 1H); $^{13}$C NMR (CDCl$_3$, 100 MHz) d 143.3, 139.0, 129.4, 127.0, 51.1, 47.3, 32.1, 22.8, 21.6, 20.5, 19.8, 19.5; MS (FAB, NBA/NaI): 288 (MNa$^+$); HRMS (FAB, NBA/NaI): calculated for $C_{14}H_{19}NO_2S$ (M+H)$^+$ 266.1215, found 266.1209; m.p. 90–91° C. (1:5=EA/hexane); Anal. Calculated for $C_{14}H_{19}NO_2S$: C, 63.37; H, 7.22, found: C, 63.54; H, 7.12.

Synthesis of 2-[[(4-Methylphenyl)sulfonyl]amino]methyl-1-heptene (6) as illustrated in FIG. 2

By-product achieved by the synthesis according to the general procedure as described above. $^1$H NMR (CDCl$_3$, 400 MHz) d 7.75 (d, J=8.0 Hz, 2H), 7.29 (d, J=8.0 Hz, 2H), 4.86 (s, 1H), 4.80 (s, 1H), 4.47 (brs, 1H), 3.49 (m, 2H), 2.41 (s, 1H), 1.95–1.20 (m, 8H), 0.85 (t, J=5.6 Hz, 3H); MS (FAB, NBA/NaI): 282 (MH+); HRMS (FAB, NBA/NaI): calculated for $C_{15}H_{23}NO_2S$ (MNa)$^+$304.1347, found 304.1359.

Synthesis of 2-Methyl-3-[(4-methylphenyl)sulfonyl]amino-1-cyclohexone (7) as illustrated in FIG. 2

By-product synthesized according to the general procedure as described above. $^1$H NMR (CDCl$_3$, 500 MHz) d 7.78 (d, J=8.5 Hz, 2H), 7.30 (d, J=8.0 Hz, 2H),, 5.53 (brs, 1H), 4.39 (d, J=8.0 Hz, 1H), 3.61 (m, 1H), 2.43 (s, 3H), 2.00–1.45 (m, 6H), 1.44 (s, 3H); $^{13}$C NMR (CDC$_1$, 125 MHz) d 143.1, 138.1, 132.0, 129.5, 127.1, 127.0, 51.9, 30.1, 24.8, 21.4, 20.6, 17.5; MS (FAB, NBA/NaI): 288 (MNa$^+$); HRMS (FAB, NBA/NaI): calculated for $C_{14}H_{19}NO_2S$ (M+H)$^+$ 266.1215, found 266.1211.

Synthesis of 1-[(4-Methylphenyl)sulfonyl]-2-aziridinemethanol as illustrated in FIG. 4, entry 6

Synthesized according to the general procedure as described above using the olefin, 2-methyl-2-propen-1-ol (Aldrich) $^1$H NMR (CDCl$_3$, 400 MHz) d 7.81 (d, J=8.3 Hz, 2H), 7.33 (d, J=8.1 Hz, 2H), 3.84 (ddd, J=12.4, 6.0, 3.0 Hz, 1H), 3.52 (ddd, J=12.3, 7.1, 5.1 Hz, 1H), 3.03–2.98 (m, 1H), 2.61 (d, J=7.1, 1H), 2.43 (s, 3H), 2.30 (d, J=4.6 Hz, 1H), 1.68 (t, J=6.6 Hz, 1H); 13C NMR (CDCl$_3$, 100 MHz) d 144.8, 134.4, 129.8, 127.9, 60.7, 40.3, 30.8, 21.6; MS (FAB, NBA/NaI): 250 (MNa$^+$); HRMS (FAB, NBA/NaI): calculated for $C_{10}H_{13}NO_3S$ (M+H)$^+$228.0694, found 228.0687.

Synthesis of 2,3-Bis[[(4-methylphenyl)sulfonyl]amino]-1-propanol

Synthesized according to the general procedure as described above the appropriate olefin. $^1$H NMR (CDCl$_3$, 400 MHz) d 7.72 (d, J=8.3 Hz, 2H), 7.64 (d, J=8.3 Hz, 2H), 7.275–7.23 (m, 4H), 5.75 (brs, 1H), 5.63–5.60 (m, 1H), 3.62–3.57 (m, 1H), 3.54–3.48 (m, 1H), 3.32–3.26 (m, 1H), 3.00–2.93 (m, 1H), 2.39 (s, 3H), 2.38 (s, 3H); $^{13}$C NMR (CDCl$_3$, 100 MHz) d 143.7, 136.9, 136.2, 129.82, 129.79, 127.1, 127.0, 61.6, 53.9, 43.6, 21.5; MS (FAB, NBA/NaI): 421 (MNa$^+$); HRMS (FAB, NBA/NaI): calculated for $C_7H_{22}N_2O_5S_2$ (M+H)$^+$399.1048, found 399.1062.

Synthesis of 3-Butyl-2-methyl-1-[(4-methylphenyl)sulfonyl]-2-aziridinemethanol as illustrated in FIG. 4, entry 4

Synthesized according to the general procedure as described above using the olefin, 2-methyl-2-hepten-1-ol. $^1$H NMR (CDCl$_3$, 400 MHz) d 7.76 (d, J=8.2 Hz, 2H), 7.26 (d, J=8.2 Hz, 2H), 4.00–3.91 (m, 2H), 3.17 (dd, J=8.8, 5.6 Hz, 1H), 2.96 (dd, J=7.8, 5.6 Hz, 1H), 2.37 (s, 3H), 1.44–1.28 (m, 2H), 1.36 (s, 3H), 1.23–1.05 (m, 4H), 0.74 (t, J=6.8 Hz, 3H); $^{13}$C NMR (CDCl$_3$, 100 MHz) d 143.8, 137.4, 129.3, 127.0, 65.5, 57.4, 50.4, 29.2, 26.6, 21.9, 21.4, 16.0, 13.7; MS (FAB, NBA/NaI): 320 (MNa$^+$); HRMS (FAB, NBA/NaI): calculated for $C_{15}H_{23}NO_3S$ (M+H)$^+$298.1477, found 298.1471.

Synthesis of 3,3-Dimethyl-1-[(4-methylphenyl)sulfonyl]-2-aziridinemethanol as illustrated in FIG. 4, entry 5

Synthesized according to the general procedure as described above using the olefin, (3-methyl-2-buten-1-ol; Aldrich) $^1$H NMR (CDCl$_3$, 400 MHz) d 7.83 (d, J=8.2 Hz, 2H), 7.31 (d, J=8.2 Hz, 2H), 3.75–3.69 (m, 1H), 3.52–3.48 (m, 1H), 3.12 (dd, J=7.3, 5.1 Hz, 1H), 2.42 (s, 3H), 1.72 (s, 3H), 1.31 (s, 4H); $^{13}$C NMR (CDCl$_3$, 100 MHz) d 144.0, 137.7, 129.6, 127.3, 60.3, 52.3, 51.8, 21.6, 21.3, 21.1; MS (FAB, NBA/NaI): 278 (MNa$^+$); HRMS (FAB, NBA/NaI):

calculated for $C_{12}H_{17}NO_3S$ (M+H)$^+$ 256.1007, found 256.1017; m.p. 63–64° C. (EA/hexane).

Synthesis of 2-Methyl-2,3-Bis[[(4-methylphenylsulfonyl]amino]-1-propanol as illustrated in FIG. 4, entry 6

Synthesized according to the general procedure as described above using the olefin, 2-propen-1-ol. $^1$H NMR (CDCl$_3$, 400 MHz) d 7.74 (d, J=8.4 Hz, 2H), 7.70 (d, J=8.3 Hz, 2H), 7.30 (d, J=8.2 Hz, 2H), 7.26 (d, J=8.3 Hz, 2H), 5.51 (m, 1H), 5.44 (bs, 1H), 3.58–3.49 (m, 2H), 3.10 (dd, J=13.8, 7.2 Hz, 1H), 3.05–2.97 (m, 2H), 2.42 (s, 3H), 2.40 (s, 3H), 0.98 (s, 3H); $^{13}$C NMR (CDCl$_3$, 100 MHz) d 143.8, 143.5, 139.5, 136.4, 129.9, 129.7, 126.9, 126.8, 66.8, 59.3, 48.6, 21.5, 19.0; MS (FAB, NBA/NaI): 435 (MNa$^+$); HRMS (FAB, NBA/NaI): calculated for $C_{18}H_{24}N_2O_5S_2$ (M+H)$^+$ 413.1205, found 413.1193.; m.p. 53–55° C.

Synthesis of 2-Methyl-1-[(4-methylphenyl)sulfonyl]-2-aziridinemethanol as illustrated in FIG. 4, entry 7

Synthesized according to the general procedure as described above using the olefin, 2-methyl-2-propen-1-ol (Aldrich); $^1$H NMR (CDCl$_3$, 400 MHz) d 7.81 (d, J=8.4 Hz, 2H), 7.31 (dd, J=8.5, 0.5 Hz, 2H), 3.83 (dd, J=12.5, 6.9 Hz, 1H), 3.68 (dd, J=12.5, 7.1 Hz, 1H), 2.60 (s, 1H), 2.52 (s, 1H), 2.42 (s, 3H), 2.37 (t, 1H), 1.63 (s, 3H); $^{13}$C NMR (CDCl$_3$, 100 MHz) d 144.2, 137.3, 129.6, 127.3, 65.1, 51.5, 38.6, 21.6, 17.1; MS (FAB, NBA/NaI): 264 (?) (MNa$^+$); HRMS (FAB, NBA/NaI): calculated for $C_{11}H_{15}NO_3S$ (M+H)$^+$ 242.0891, found 242.0848.

Synthesis of trans-1-[(4-Methylphenyl)sulfonyl]-3-propyl-2-aziridinemethanol as illustrated in FIG. 4, entry 1

Synthesized according to the general procedure as described above using the olefin, (trans-2-Hexen-1-ol; Aldrich) $^1$H NMR (CDCl$_3$, 400 MHz) d 7.82 (d, J=8.3 Hz, 2H), 7.31 (d, J=8.1 Hz, 2H), 4.07 (m, 1H), 3.86 (m, 1H), 2.93 (m, 2H), 2.68 (br, 1H), 2.42 (s, 3H), 1.58–1.42 (m, 2H), 1.26 (dt , J=14.9, 7.5 Hz, 2H), 0.85 (t, J=7.4 Hz, 3H); $^{13}$C NMR (CDCl$_3$, 100 MHz) d 144.2, 137.1, 129.6, 127.3, 60.9, 51.7, 46.2, 32.2, 21.6, 20.4, 13.5; MS (FAB, NBA/NaI): 292 (MNa$^+$); HRMS (FAB, NBA/NaI): calculated for $C_{13}H_{19}NO_3S$ (M+Na)$^+$: 292.0983, found: 292.0991.

Synthesis of trans-1-[(4-Methylphenyl)sulfonyl]-3-phenyl-2-aziridinemethanol as illustrated in FIG. 4, entry 3

Synthesized according to the general procedure as described above using the olefin, 2-methyl-2-hepten-1-ol (Aldrich) $^1$H NMR (CDCl$_3$, 400 MHz) d 7.81 (d, J=8.3 Hz, 2H), 7.28–7.23 (m, 5H), 7.14–7.10 (m, 2H), 4.31 (ddd, J=13.5, 10.2, 2.9 Hz, 1H), 4.16 (ddd, J=13.5, 8.6, 4.8 Hz, 1H), 4.01 (d, J=4.4 Hz, 1H), 3.17 (ddd, J=7.9, 3.7, 1.4 Hz, 1H), 3.12 (dd, J=10.0, 4.8 Hz, 1H), 2.39 (s, 3H); $^{13}$C NMR (CDCl$_3$, 100 MHz) d 144.4, 137.0, 134.5, 129.7, 128.6, 128.4, 127.1, 126.4, 60.7, 54.8, 46.3, 21.6; MS (FAB, NBA/NaI): 326 (MNa$^+$); HRMS (FAB, NBA/NaI): calculated for $C_{16}H_{17}NO_3S$ (M+Na)$^+$: 326.0827, found: 326.0814.

Synthesis of cis-1-[(4-Methylphenyl)sulfonyl]-3-propyl-2-aziridinemethanol as illustrated in FIG. 4, entry 2

Synthesized according to the general procedure as described above using the olefin, cis-2-hexen-1-ol (Aldrich) $^1$H NMR (CDCl$_3$, 400 MHz) d 7.78 (d, J=8.3 Hz, 2H), 7.30 (d, J=8.1 Hz, 2H), 3.70 (m, 1H), 3.57 (m, 1H), 2.99 (m, 1H), 2.78 (m, 1H), 2.40 (s, 3H), 2.20 (brs, 1H), 1.48–1.17 (m, 4H), 0.81 (t, J=7.3 Hz, 3H); $^{13}$C NMR (CDCl$_3$, 100 MHz) d 144.6, 134.4, 129.6, 128.0, 59.3, 44.9, 44.6, 28.7, 21.6, 20.5, 13.5; MS (FAB, NBA/NaI): 292 (MNa$^+$); HRMS (FAB, NBA/NaI): calculated for $C_{13}H_{19}NO_3S$ (M+Na)$^+$: 292.0983, found: 292.0989.

Synthesis of 3-Benzyloxymethyl-1-[(4-methylphenyl) sulfonyl]-2-aziridinemethanol as illustrated in FIG. 4, entry 8

Synthesized according to the general procedure as described above using the olefin, cis-4-benzyloxy-2-buten-1-ol (Aldrich) $^1$H NMR (CDCl$_3$, 400 MHz) d 7.81 (d, J=8.3 Hz, 2H), 7.32–7.23 (m, 5H), 7.19–7.15 (m, 2H), 4.42 and 4.37 (two d, J$_{AB}$=11.8, 1H each), 3.66–3.52 (m, 4H), 3.07 (m, 2H), 2.86 (br, 1H), 2.37 (s, 3H); $^{13}$C NMR (CDCl$_3$, 100 MHz) d 144.6, 137.1, 134.0, 129.5, 128.2, 127.8, 127.6, 127.4, 72.8, 66.3, 59.0, 43.1, 42.3, 21.4; MS (FAB, NBA/NaI): 370 (MNa$^+$); HRMS (FAB, NBA/NaI): calculated for $C_{18}H_{21}NO_4S$ (M+Na)$^+$: 370.1089, found: 370.1079.

Synthesis of syn-7-[(4-Methylphenyl)sulfonyl]-7-azabicyclo[4.1.0]heptan-2-ol as illustrated in FIG. 4, entry 9

Synthesized according to the general procedure as described above using the olefin, 2-cyclohexen-1-ol, Aldrich. $^1$H NMR (CDCl$_3$, 400 MHz) d 7.82 (d, J=8.4 Hz, 2H), 7.33 (d, J=8.1 Hz, 2H), 3.93 (brs, 1H), 3.18 (m, 2H), 2.43 (s, 3H) 1.80–1.15 (m, 7H); $^1$H NMR (C$_6$D$_6$, 400 MHz) d 7.87 (J=8.4 Hz, 2H), 6.73 (d, J=8.6 Hz, 2H), 3.48 (m, 1H), 3.02 (dd, J=7.0, 4.2 Hz, 1H) 2.92 (m, 1H), 1.80 (s, 3H), 1.48–1.02 (m, 7H); $^{13}$C NMR (CDCl$_3$, 100 MHz) d 144.7, 134.7, 129.8, 127.9, 64.6, 44.4, 42.5, 29.1, 21.8, 21.7, 18.4; MS (FAB, NBA/NaI): 290 (MNa$^+$); HRMS (FAB, NBA/NaI) : calculated for $C_{13}H_{17}NO_3S$ (M+H)$^+$: 268.1007, found: 268.0999.

Synthesis of anti-7-[(4-Methylphenyl)sulfonyl]-7-azabicyclo[4.1.0]heptan-2-ol

Synthesized according to the general procedure as described above using the appropriate olefin. $^1$H NMR (CDCl$_3$, 400 MHz) d 7.79 (d, J 8.3 Hz, 2H), 7.31 (d, J=8.2 Hz, 2H), 3.95–3.91 (m, 1H), 3.05–3.02 (m, 1H), 2.92 (d, J=6.8 Hz, 1H), 2.42 (s, 3H), 1.90 (d, J=4.8 Hz, 1H), 1.82–1.75 (m, 3H), 1.48–1.38 (m, 1H), 1.25–1.10 (m, 2H).

Figure 6:
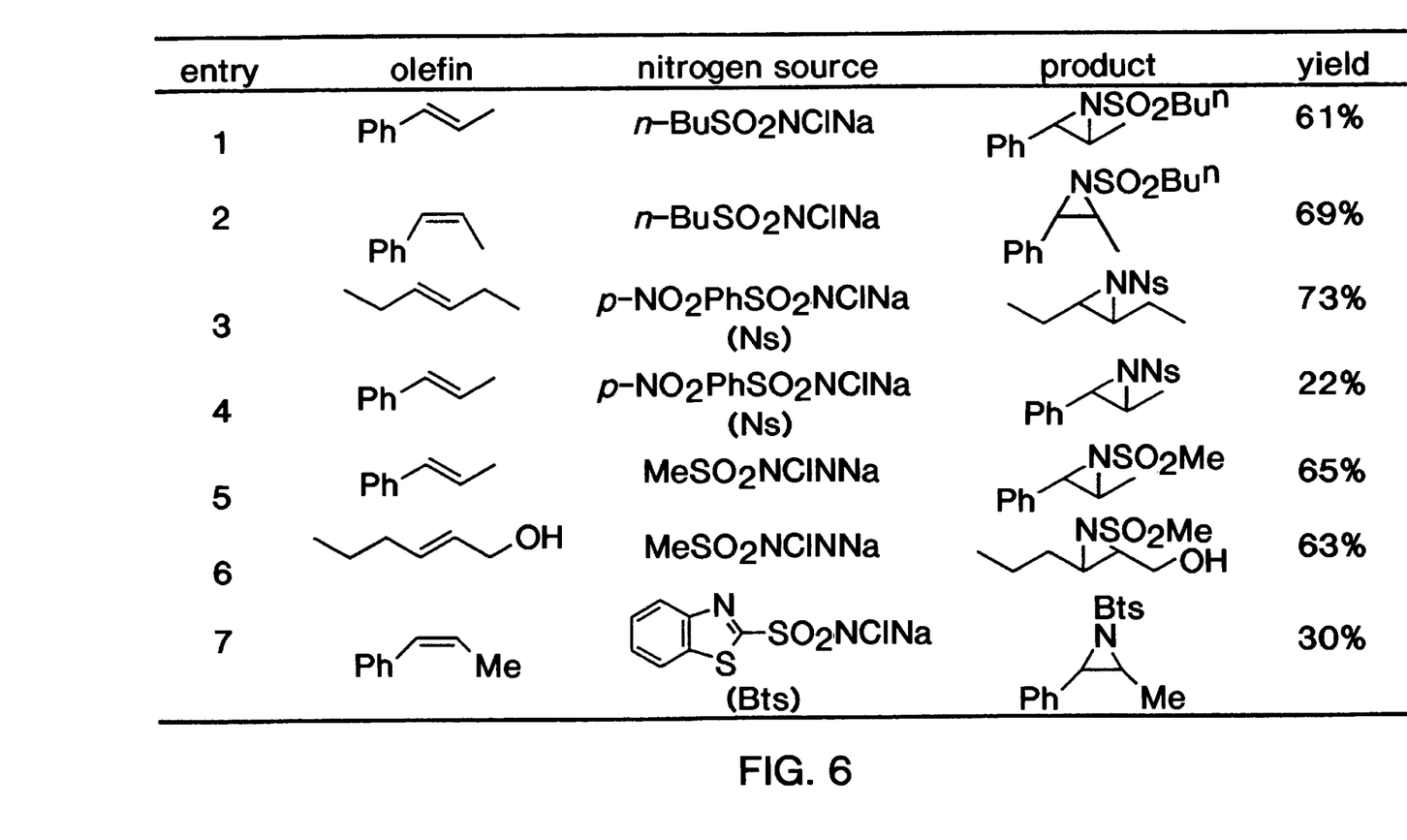
FIG. 6 provides representative examples of 1,2-disubstituted olefins using other nitrogen sources.

Synthesis of aziridines using dienes and allylic alcohols as shown in FIGS. 6–7

Synthesized according to the general procedure as described above using the respective olefins and nitrogen source. The olefins are commercially available as follows: (all separate reactions): 2-cyclohexen-1-ol (Alrich; entry 1); trans-1,4-hexadiene (ChemSampC); 2,4-hexadiene (ChemSampC); 2,7-octadien-1-ol; trans-2-cis-6-nonadien-1-ol; 1,4-cyclohexadiene, etc.

There are two general methods to prepare N-sodio-N-chloro sulfonamides from sulfonamide Method 1: Heintzelman et al. *Synthesis* 1976, 731.

Method 2: Rudolph et al. *Angew. Chem. Int. Ed. Engl.* 1996, 35, 2810.

It is emphasized that while a preferred form of the invention has been shown in the specification, drawings and described, since variations in the preferred form will be apparent to those skilled in the art (see above discussion for ranges of substrates and scope of olefins employable with the claimed method), the invention should not be construed as limited to the specific form shown and described, but instead is as set forth in the following claims.

What is claimed:

1. A one pot method for synthesizing an aziridine from an olefin comprising the step of catalyzing the addition of a nitrogen source to said olefin with a catalytic amount of phenyltrimethylammonium tribromide as the catalyst for producing the aziridine.

2. The one pot method for synthesizing an aziridine from an olefin and a nitrogen source as described in claim 1 wherein the nitrogen source is a N-sodio-N-chloro-sulfonamide.

3. The one pot method for synthesizing an aziridine from an olefin and a nitrogen source as described in claim 2 wherein the N-sodio-N-chloro-sulfonamide is selected from a group consisting of p-NO$_2$PhSO$_2$NClNa, n-BuSO$_2$NClNa, MeSO$_2$NClNa, t-BuSO$_2$NClNa, and an N-sodio-N-chloro salt of a sulfonamide represented by one of the following structures:

wherein R, R' and R" are each independently a radical selected from a group consisting of hydrogen, —O—(C$_1$–C$_6$ alkyl), —(C$_1$–C$_6$ alkyl), —O-benzyl, —O-phenyl, —NO$_2$, —Cl, —Br, —I, methyl; methoxy, t-Butyl, and CF$_3$.

4. The one pot method for synthesizing an aziridine from an olefin and a nitrogen source as described in claim 3 wherein an organic solvent is selected from a group consisting of acetonitrile, DMF, DMSC, THF, acetonitrile and water cosolvent, acetonitrile and DMF cosolvent, acetonitrile and DMSO cosolvent and acetonitrile and THF cosolvent.

5. The one pot method for synthesizing an aziridine from an olefin and a nitrogen source as described in claim 3 comprising the following steps:

Step A: Admixing said olefin with a nitrogen source and an organic solvent for forming a reaction mixture; then Step B: Catalyzing the addition of the nitrogen source to the olefin of said Step A with phenyltrimethylammonium tribromide as the catalyst wherein a bromide group of the catalyst adds beta to the nitrogen group of said nitrogen source for forming a β-bromo-N-substituted intermediate; then Step C: Cyclizing the 5-bromo-N-substituted intermediate of said step B by intramolecular displacement of the β-bromo group with the nitrogen group of said β-bromo-N-substituted intermediate for forming the aziridine.

* * * * *